United States Patent [19]
Fox

[11] Patent Number: 6,066,116
[45] Date of Patent: May 23, 2000

[54] ADJUSTABLE INTRAVENOUS INJECTION AID

[75] Inventor: Melvin D. Fox, 6343 Yeagerstown Rd., New Market, Md. 21774

[73] Assignee: Melvin D. Fox, New Market, Md.

[21] Appl. No.: 08/818,128

[22] Filed: Mar. 14, 1997

[51] Int. Cl.[7] .................................................. A61M 5/00
[52] U.S. Cl. ........................ 604/115; 604/134; 128/877
[58] Field of Search ................................... 128/846, 877, 128/878, 879; 604/115, 116, 250; 602/20–22

[56] References Cited

U.S. PATENT DOCUMENTS

| | | | |
|---|---|---|---|
| 3,324,854 | 6/1967 | Weese | 604/115 |
| 4,403,987 | 9/1983 | Gottinger | 604/115 |
| 4,586,924 | 5/1986 | Lanning | 604/115 |
| 5,254,095 | 10/1993 | Harvey | 604/115 |

Primary Examiner—Michael A. Brown

[57] ABSTRACT

A device is disclosed which aids in the stabilization of veins for puncturing. A device body is disclosed which may be constructed of any suitable lightweight and durable metal or resinous material which may be easily cast or formed and which possesses properties of strength and resiliency. A handle with a grip extending outwardly from the device body when said device is in the operative position may be engaged by a user's thumb or forefinger to stabilize the device body during use. A pair of elongated flanges displaced outwardly from the centerline of the device, spaced apart a selected distance, and terminating in contact surfaces, may be placed such that the subject vein may extend through a space present between the contact surfaces of the elongated flanges. The device may further have an adjuster disposed upon the pair of elongated flanges for adjusting the distance between elongated flanges causing the distance between the ends of the elongated flanges to increase or decrease thus accommodating veins of different sizes.

11 Claims, 4 Drawing Sheets

107

ADJUSTABLE INTRAVENOUS INJECTION AID

FIELD OF THE INVENTION

The present invention relates to an apparatus for assisting in the introduction of intravenous devices into the vein of a subject or patient. In particular, the present invention is directed to a device for stabilizing subject veins of different sizes for the purpose of inserting an intravenous injection apparatus into a subject vein.

BACKGROUND OF THE INVENTION

In the fields of medicine and general research it is often necessary to provide injections of medicinal fluids or take fluid samples from a mammalian patient or subject and in particular a human. Injection may be by way of an IV needle, hypodermic injection and the like. For placement of injection needles of any kind, complications may arise when the subject of the injection is a vein.

Veins may be distinguished from arteries in that veins carry blood which has been spent of oxygen and return spent blood to the heart. Veins may typically have less pressure than arteries and are often more problematic for injection purposes.

Since veins carry exhausted blood at a lower pressure, veins do not "stand out" as readily for injection purposes as do arteries and accordingly do not provide as stable a surface to push against during the initial insertion of a needle or other injection means. Veins may move position, may be different in position from one subject to another, and may collapse if traumatized severely enough by repeated injection attempts. Because of movement, veins may be missed altogether. Improper insertion pressure due to sudden vein movement or uncertain placement may cause a needle or other means to penetrate both sides of the vein.

Because of the risk of discomfort to the patient and possible damage to veinous and surrounding tissues, trained technicians are often used to administer injections and IVs. While a significant amount of skill is necessary, devices which assist the process of injection are often used. These devices range in type and complexity but are accompanied by disadvantages.

Harvey (U.S. Pat. No. 5,254,095) discloses a vein tenter which may be used to pinch a portion of skin under which a vein may be positioned. Harvey's device may be positioned at various angles relative to a subject vein in order to facilitate puncturing the vein. Harvey's device however requires constant pinching pressure by the user in order to maintain a hold upon the device. If a user momentarily releases pressure on the device, the device may lose its position on the subject vein possibly causing damage or slippage of the injection device.

Gubich (U.S. Pat. No. 5,147,306) discloses a device for puckering flesh in order to facilitate injections. Gubich's device facilitates self-injection using spring biased jaws forming a clamp, which can be opened by applying pressure to jaw ends with a thumb and forefinger, displacing the device upon a subject vein and closed by relieving pressure between the thumb and forefinger. Gubich's device however, does not account for veins of different sizes and may apply different pressures depending on the size and location of the vein to be punctured. Constant pinching pressure from the Gubich device may also cause discomfort on some patients and may cut off blood flow in the subject vein on others.

Other devices are available which provide varying degrees of success for stabilizing veins for puncture, yet all having disadvantages. While some devices consist of complicated straps and guides, others may be simpler yet fail to accommodate veins of different sizes. It would be desirable therefore to have a device that is capable of stabilizing veins for puncture, easy to use, simple in construction, and yet capable of accommodating veins of different sizes with a consistent level of comfort to the patient or subject.

SUMMARY OF THE INVENTION

A device is disclosed that aids in the stabilization of veins for puncturing. Veins may be punctured for introducing or extracting fluids including medicines, nutrients, bodily fluids, saline, and tracing agents. Operators of the disclosed device may include a technician, a doctor, a nurse, or the subject or patient themselves and may also include a lay person.

The device of the present invention comprises an device body that may be constructed of any suitable metal or resinous material, be easily cast or formed and possess properties of strength and resiliency. The device may be constructed of any such materials capable of withstanding repeated bending during use, yet are lightweight and durable.

The device of the present invention may have a handle with a grip extending outwardly from the device body. The grip may be positioned between the handle and an operative end of the device body. The grip may be engaged by a user's thumb or forefinger to stabilize the device during use and generally extends outwardly on a side of the device opposite to the operative side of the device relative to the centerline of the device, that is, the side which is toward the subject. A pair of elongated flanges may form the operative end of the device and may be spaced outwardly from a center line a selected distance. For ease of placement of the device on a subject, the elongated flanges may be disposed away from the center line of the device toward the operative side by an amount sufficient to overcome the space required for the device to be gripped by the handle. Deployment of the deivce in the operative position occurs when the device is grasped by a user and the elongated flanges are placed against the skin of the patient or subject in the vicinity of the subject vein. The device may be placed such that the subject vein may extend through a space present between the elongated flanges. The device may be placed such that the axis of the device and the axis of the portion of the vein that the user wishes to puncture are parallel.

The device may further have an adjuster disposed upon the pair of elongated flanges for adjusting the distance between individual elongated flanges. The adjuster may be adjusted forwardly and backwardly having the effect of constricting more or less the outwardly biased elongated flanges causing the distance between the ends of the elongated flanges to increase or decrease thus accommodating veins of different sizes.

DETAILED DESCRIPTION OF THE DRAWINGS

Figure 1:
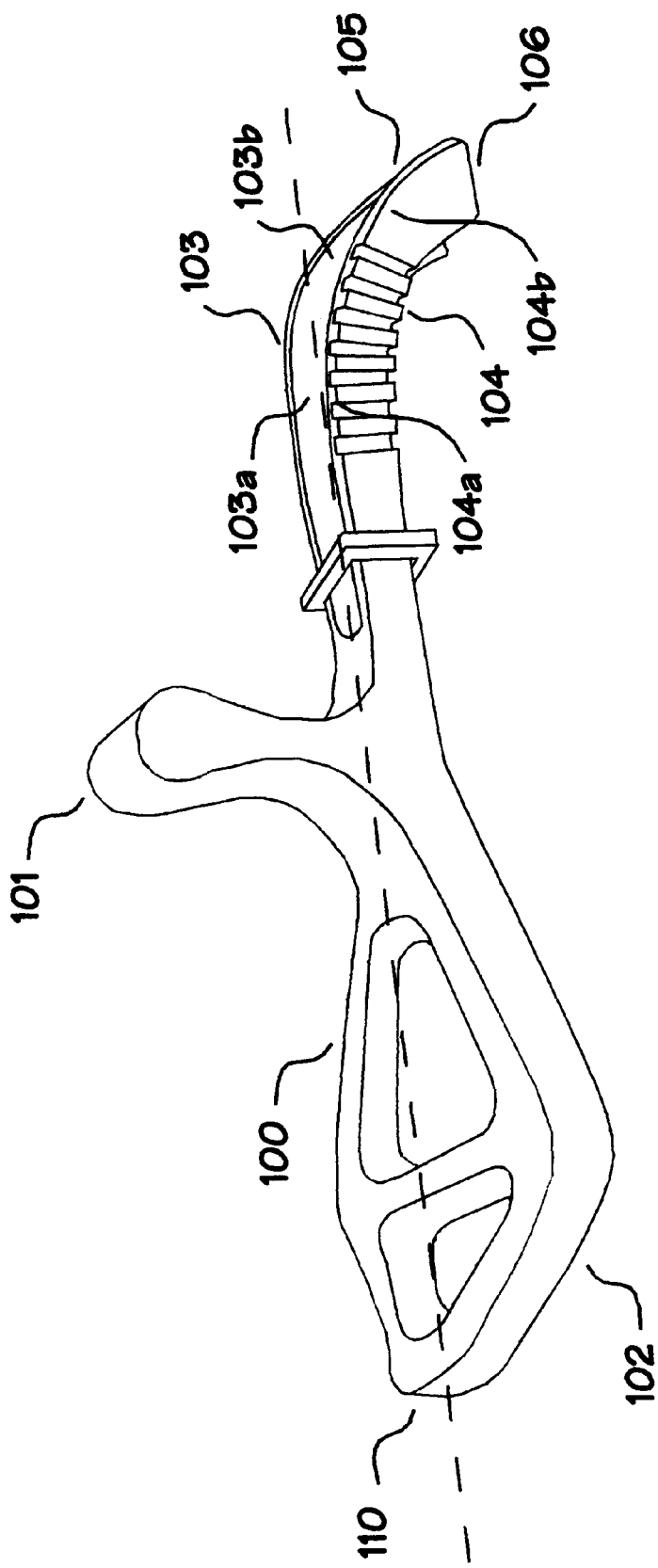
FIG. 1 is a perpsective view illustrating the device of the present invention.

The device of the present invention is shown in FIG. 1. The device of the present invention may have a body 100 constructed by forming any suitably deformable lightweight material including metal or resinous material such as thermoplastic or the like. Body 100 may further be cast from thermoplastic or lightweight metal. Thermoplastic construction may be most desirable in the preferred embodiment since it is relatively inexpensive and easily formed or cast. Body 100 forms the central element of the hand held device of the present invention which can be grasped in the hand by way of a handle, stabilized with a grip formed of an outwardly projecting post located near the center of the device, adjusted using a slidable adjuster located near the front of the device, and displaced on a subject.

Grip 101 may be a cylindrical post, rectangular member, or ring projecting outwardly from body 100. Grip 101 projects perpendicularly from the center line of body 100 a distance adequate to accomodate a finger or thumb and may be used to stabilize a user's grip during deployment. Grip 101 may be located at a point between handle 102 disposed at one end of body 100 and an operative end of body 100 disposed at the end opposite to handle 102. The operative end of the device of the present invention may be deployed by grasping handle 102 and stabilizing the device with a forefinger placed on grip 101, a forefinger wrapped around grip 101 or a thumb placed on grip 101, or like configuration depending on what is comfortable to the user. Forming the operative end of body 100 are elongated flanges 103 and 104 which project along centerline 110 and then bend away from centerline 110 to form the operative end of the device.

Elongated flanges 103 and 104 may be formed by cutting along the centerline of a piece of cylindrical stock of which device 100 may be formed and displacing the flanges outwardly. In the preferred embodiment of the present invention, elongated flanges 103 and 104 may be biased outwardly providing tension against which an adjusting mechanism may operate. Outward bias may be provided by forming elongated flanges 103 and 104 such that they are displaced outwardly. The outward displacement of flanges 103 and 104 in combination with the natural resiliency of the material from which they are formed may create a bias against inward displacement. Outward bias upon elongated flanges 103 and 104 may further be provided using a conventional spring mechanism or the like not shown.

Figure 2:
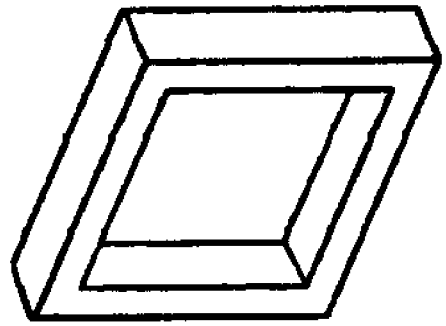
FIG. 2 is a perspective view of the adjuster of the present invention.

Adjuster 107 shown in FIG. 2 may be substantially U-shaped and has oppositely directed projections 107a and 107b for grasping the underside of flanges 103 and 104. Tab 107c projects downwardly into the center of the adjuster 107 for maintaining sliding contact with the inside surfaces 103a and 104a of flages 103 and 104. By adjusting the position of adjuster 107, the distance between elongated flanges 103 and 104 may be regulated and veins of different sizes may be accommodated.

Figure 3:
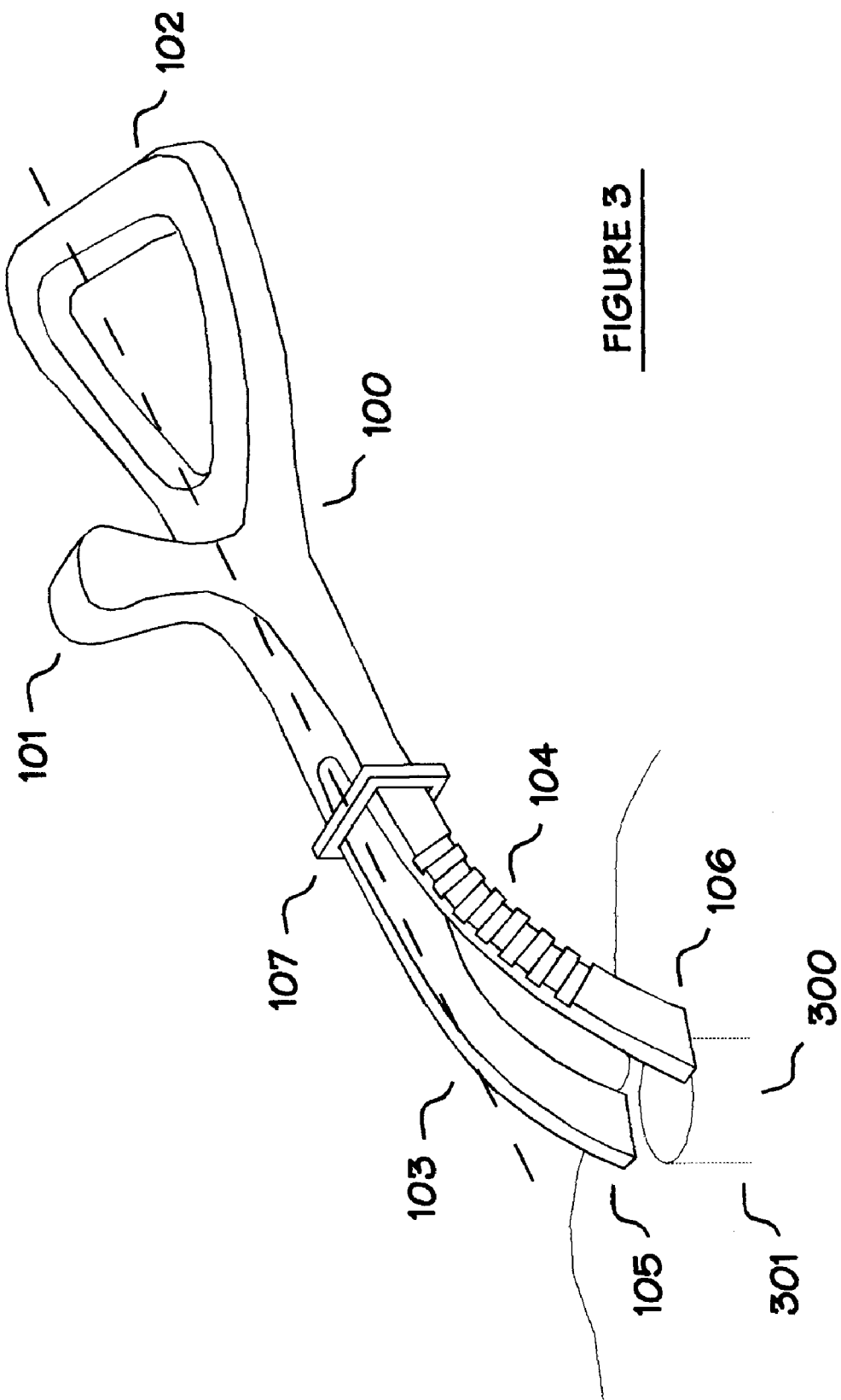
FIG. 3 is a perspective view of the device of the present invention deployed upon a subject vein.

Body 100 of the present invention is shaped with a concave surface creating a more favorable relation between flanges 103 and 104 for the purpose of deploying the device on a subject vein as best shown in FIGS. 1 and 3. Flanges 103 and 104 are each curved at their respective ends 103b and 104b to form contact surfaces 105 and 106 which may create constraints on the lateral movement of a subject vein. Contact surfaces 105 and 106 may be shaped to create the kind of pressure desired on the skin adjacent to subject vein 300 as shown in FIG. 3. The shape of contact surfaces 105 and 106 may include a rounded shape, a flat shape, and a diagonal shape with an edge substantially parallel to the skin surface of the subject upon which said device is deployed. Contact surfaces 105 and 106 may be seen to be displaced at a distance 301 around subject vein 300. Such shaping may be accomplished by various machining processes performed on the unfinished ends of flanges 103 and 104 in the case of integral construction using cylindrical stock or may be accomplished by shaping a mold accordingly for cast construction.

Figure 4:
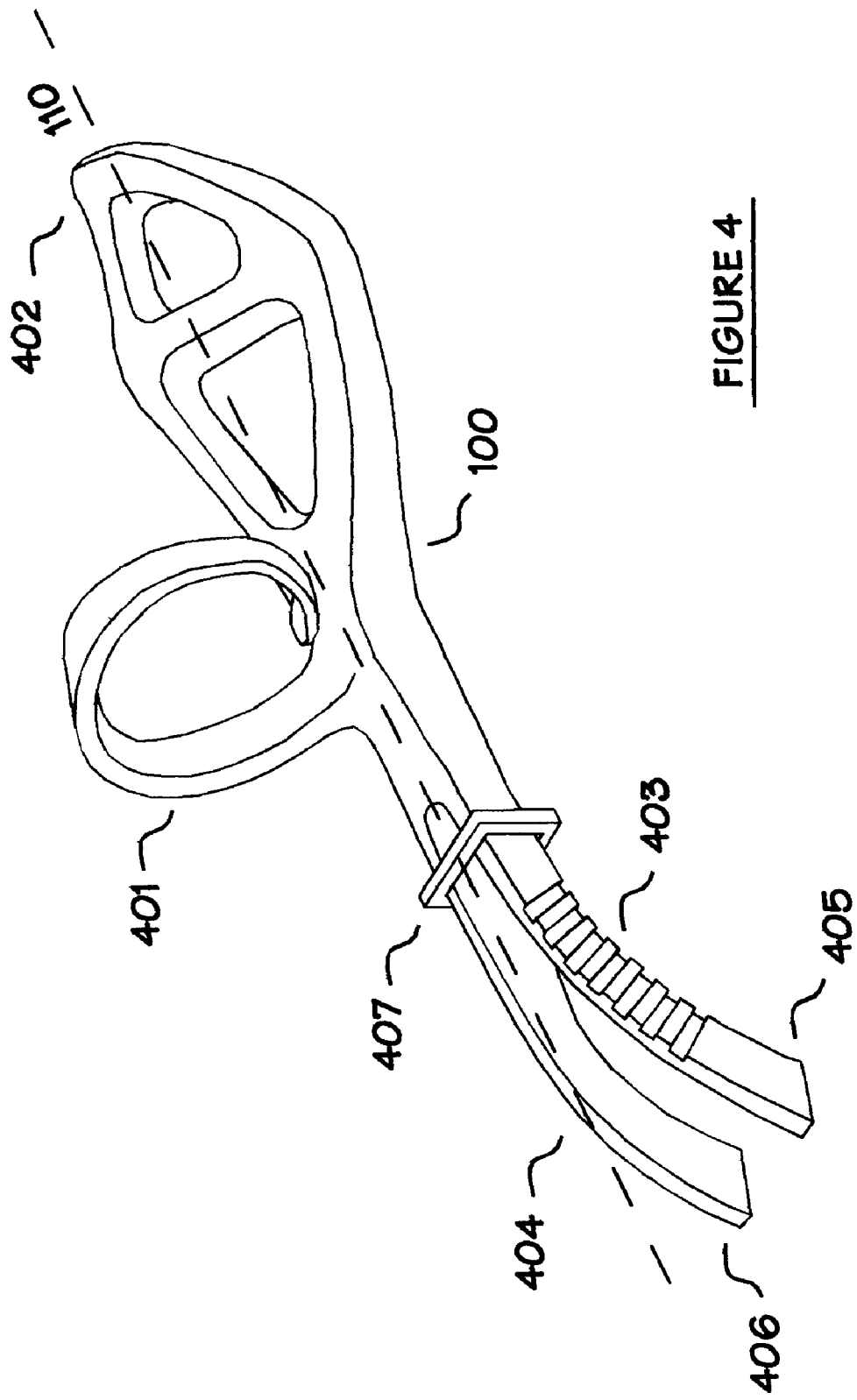
FIG. 4 is a perspective view illustrating an alternative embodiment of the present invention.

In an alternative embodiment as shown in FIG. 4, the present invention may be formed from a continuous section of cylindrical resinous stock. Forming may begin at either the operative end of body 100 or at the end of a loop which forms grip 401. Starting at grip 401, a loop may be formed by bending a section of cylindrical stock into a loop of a diameter approximately half the distance between grip 104 and the end of handle 402 or more or less accordingly to accomodate an average thumb or forefinger.

The standing end of cylindrical stock may then be extended along center line 110 roughly perpendicular and away from grip 401 to begin forming handle 402. Handle 402 may be formed by making a semicircular bend in cylindrical stock at a point sufficient to accomodate the size of an average hand and bringing the standing end of cylindrical stock back toward grip 401. At the portion of body 100 where the end of the loop forming grip 401 and handle 402 meet, cylindrical stock may be glued or otherwise suitably joined or fused by a heat process or the like.

Finally, the operative end of body 100 may be formed by extending the remaining end of cylindrical stock away from handle 402 along centerline 110. Elongated flanges 403 and 404 may be formed by cutting the cylindrical stock down centerline 110 and diplacing elongated flanges 403 and 404 outwardly. Contact surfaces 406 and 405 may be bent slightly away from centerline 110 to make them more easily deployable upon a subject vein. Contact surfaces 406 and 405 may further be finished on their ends by smoothing and flattening into an optimum shape which may include a rounded shape, a flattened shape or the like. While the foregoing describes its preferred and alternative embodiments, it may be appreciated by those skilled in the art that similar constructions may be employed without departing from the spirit and scope of the present invention.

I claim:

1. A device for stabilizing a vein to permit puncturing and transfer of a fluid therein, said device comprising:

a body having an operative end and a substantially concave shaped;

a handle integral to said body for holding said device;

a grip integral to and extending outwardly from said body, said grip positioned between said handle and said operative end of said body, said grip for stabilizing said device during operation;

a pair of elongated flanges forming said operative end of said body, said pair of elongated flanges integral to said body and mutually spaced apart a selected distance, to accommodate the size of said vein, said elongated flanges for engaging and constraining the lateral movement of said vein, said pair of elongated flanges mutually spaced outwardly from the center line of said body; and an adjuster disposed upon said pair of elongated flanges for selectively adjusting said selected distance between said pair of elongated flanges and allowing said device to be accurately disposed upon said vein for stabilizing said vein.

2. A device according to claim 1 wherein said grip further comprises a straight section extending outwardly from said body.

3. A device according to claim 2 wherein said straight section comprises a rounded cross section.

4. A device according to claim 2 wherein said straight section comprises a rectangular cross section.

5. A device according to claim 1 wherein said grip further comprises a ring shape.

6. A device according to claim 1 wherein said operative end is displaced outwardly from a longitudinal centerline of said body for improving placement of said operative end upon said vein.

7. A device according to claim 6 wherein said pair of elongated flanges further comprises a pair of contact surfaces wherein each contact surface in said pair of contact surfaces is located at an end of each flange in said pair of elongated flanges.

8. A device according to claim 7 wherein said contact surfaces are rounded.

9. A device according to claim 7 wherein said contact surfaces are flat and perpendicular to a central axis.

10. A device according to claim 7 wherein said contact surfaces are angled with respect to a central axis.

11. A device for stabilizing a vein to permit puncturing and transfer of a fluid therein, said device comprising:

a body having an operative end and substantially concave shaped;

a handle integral to said body;

a grip integral to and extending outwardly from said body, said grip positioned between said handle and said operative end of said body;

a pair of elongated flanges forming said operative end of said body, said pair of elongated flanges integral to said body and mutually spaced apart a selected distance, said pair of elongated flanges mutually spaced outwardly from the center line of said body, said pair of elongated flanges being further displaced from said center line in a direction away from said grip member; and an adjuster disposed upon said pair of elongated flanges for adjusting said selected distance between said pair of elongated flanges and allowing said device to be accurately disposed upon said vein for stabilizing said vein, said adjuster comprising an annular band disposed around said elongated flanges wherein said elongated flanges are biased outwardly, said adjuster being slidable forwardly or rearwardly to overcome said outward bias and thereby varying the magnitude of said selected distance.

* * * * *